(12) United States Patent
Polwart et al.

(10) Patent No.: US 8,101,137 B2
(45) Date of Patent: Jan. 24, 2012

(54) ANALYSIS INSTRUMENT

(75) Inventors: Stuart Polwart, Stirlingshire (GB); Joel Fearnley, Peebleshire (GB); Kenneth G. Macnamara, Edinburgh (GB); Urs Lamb, Edinburgh (GB)

(73) Assignee: Lab901 Limited, Midlothian (GB)

( * ) Notice: Subject to any disclaimer, the term of this patent is extended or adjusted under 35 U.S.C. 154(b) by 1078 days.

(21) Appl. No.: 11/815,852

(22) PCT Filed: Feb. 8, 2006

(86) PCT No.: PCT/GB2006/000444
§ 371 (c)(1),
(2), (4) Date: Dec. 10, 2007

(87) PCT Pub. No.: WO2006/085071
PCT Pub. Date: Aug. 17, 2006

(65) Prior Publication Data
US 2010/0126857 A1    May 27, 2010

(30) Foreign Application Priority Data
Feb. 8, 2005  (GB) .................................. 0502556.4

(51) Int. Cl.
*G01N 27/26* (2006.01)
*B01L 3/00* (2006.01)
(52) U.S. Cl. ........ 422/504; 204/604; 204/453; 422/403; 422/412; 422/82; 73/864.91
(58) Field of Classification Search .......... 204/600–650, 204/450, 453; 422/100, 99, 400–430, 500–570, 422/82; 73/864.91
See application file for complete search history.

(56) References Cited

U.S. PATENT DOCUMENTS

| 5,284,570 | A | 2/1994 | Savage et al. |
| 2001/0005489 | A1 | 6/2001 | Roach et al. |
| 2001/0020588 | A1 | 9/2001 | Adourian et al. |
| 2003/0062265 | A1* | 4/2003 | King et al. ............. 204/453 |
| 2005/0231723 | A1* | 10/2005 | Blasenheim et al. ..... 356/414 |
| 2006/0032746 | A1* | 2/2006 | Knott et al. ............ 204/450 |

FOREIGN PATENT DOCUMENTS

| EP | 1 388 369 | 2/2004 |
| WO | WO 01/30490 | 5/2001 |
| WO | WO 03/045557 | 6/2003 |
| WO | WO 2004/071660 | 8/2004 |

OTHER PUBLICATIONS
International Search Report dated Sep. 11, 2006.

* cited by examiner

*Primary Examiner* — Jeffrey T Barton
*Assistant Examiner* — Jennifer Dieterle

(57) ABSTRACT

An analysis instrument for processing a microfluidic device, having sample storage means, a microfluidic device holder, sample loading means for loading sample into a microfluidic device disposed in the holder, processing means for enabling a reaction in a microfluidic device, and detection means for detecting and/or measuring the reaction is disclosed. The microfluidic device holder is adapted to hold the microfluidic device including a tape in position for processing and/or detection. A microfluidic processing device is also disclosed which includes a reaction chamber, and a sample loading chamber into which a sample is injectable. The reaction chamber is operatively connected to the sample loading chamber. A cover extends across at least part of the sample loading chamber. The cover and the reaction chamber include pierceable material and are separated by an overspill cavity configured to accept any overspill of an injected sample. A kit is also disclosed which has the analysis instrument and the microfluidic processing device as described above.

7 Claims, 14 Drawing Sheets

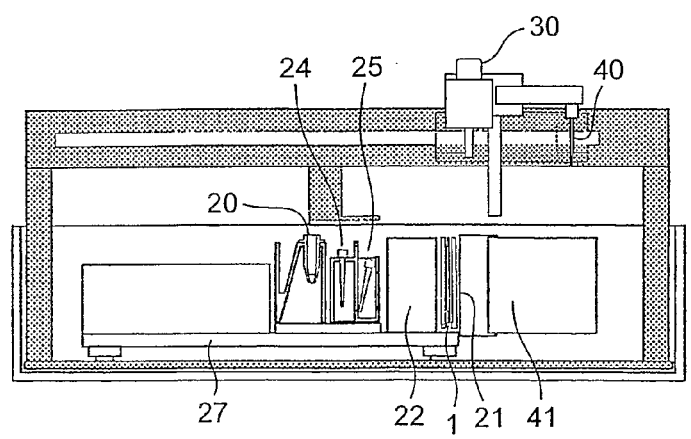
FIG. 4A
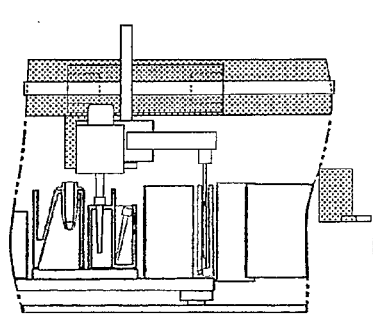     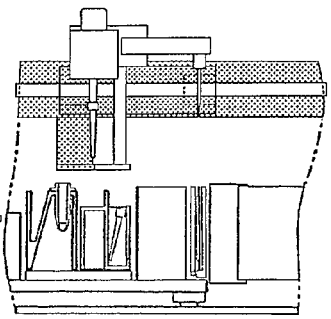     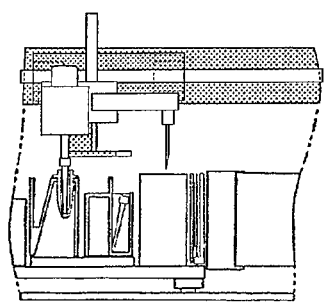
   FIG. 4B              FIG. 4C              FIG. 4D
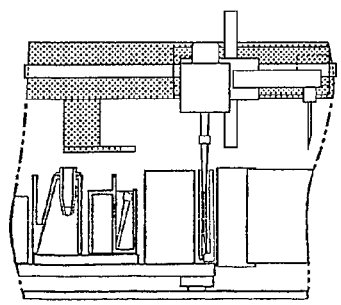     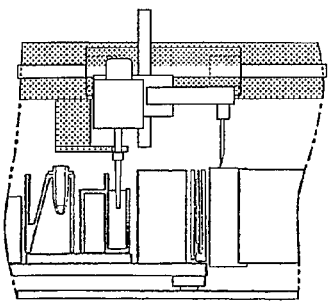     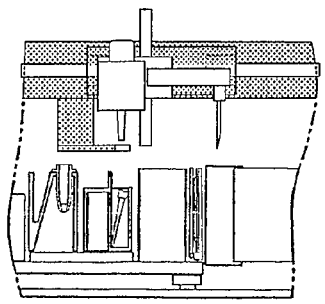
   FIG. 4E              FIG. 4F              FIG. 4G

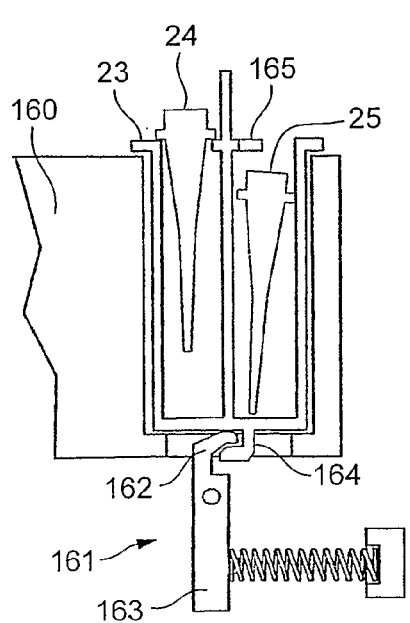
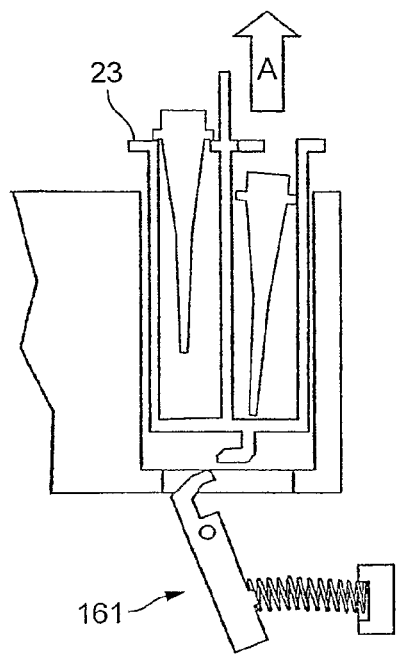
FIG. 6A   FIG. 6B
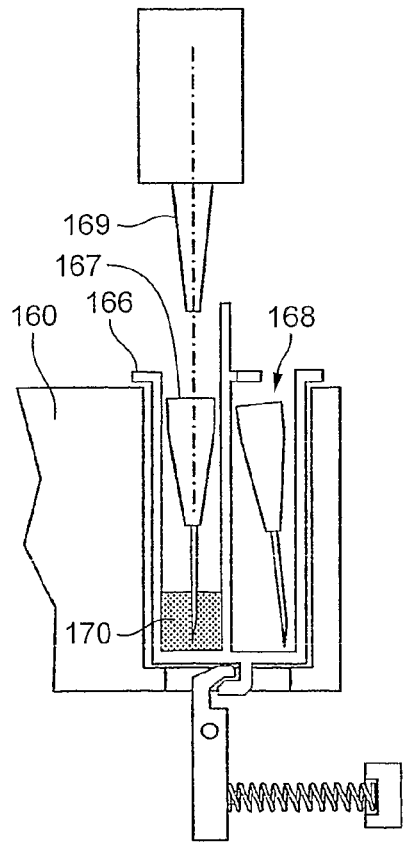
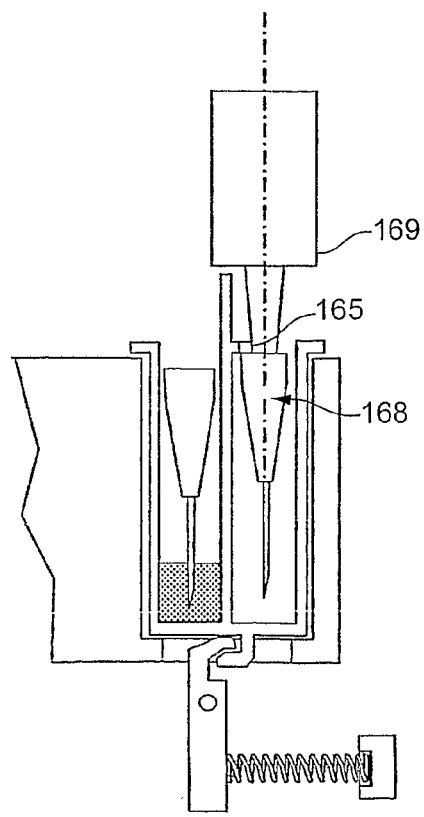
FIG. 6C   FIG. 6D

ANALYSIS INSTRUMENT

RELATED APPLICATIONS

This application is the U.S. National phase under 35 U.S.C. §371 of International Application PCT/GB2006/000444, filed Feb. 8, 2006, which claims priority to GB 0502556.4, filed Feb. 8, 2005.

The present invention relates to an analysis instrument for use in the determination of properties of biological and/or biochemical samples using a variety of techniques including immunoassay, cell based assay and PCR. In particular, the invention relates to the analysis of samples containing RNA, DNA or proteins using an electrophoresis process.

BACKGROUND

There are a large number of analysis instruments and equipment available. Analysis of biological samples continues to be extensively done on a macro scale and frequently requires a large number of process steps.

One of the most extensively used analysis techniques within the life sciences laboratory is gel bath based electrophoresis. This process enables separation of a complex mixture of charged molecules, such as nucleic acids or proteins, according to their electro-phoretic mobility. Following this method, the relative molecular weight and amounts of the constituent molecules can be determined. However, this well established technique is time consuming, labour intensive and requires significant amounts of bench space. Sample preparation, sample analysis and sample clean-up all involve wet chemistry in which some of the reagents used (e.g. ethidium bromide) are toxic, and require specialised handling and disposal methods.

A common operating configuration for the electrophoresis and analysis of DNA fragments using a slab gel includes:
an ultra pure demineralised water supply;
bulk supply bottles of buffer reagent;
chemical stains or dyes;
gel powder;
laboratory glassware for gel preparation;
a heating and stirring device for gel preparation (mix powder with buffer);
a gel tank and all its accessory parts;
an electrical power supply unit;
a sample loading pipette;
a light box on to which the processed gel is transferred such that the fluorochromes in the gel can be activated; and
a gel camera, the most basic arrangement of which would be an instant camera attached to a metal hood which can be fitted in a light tight arrangement to the light box.

Available improvements to this traditional process are:
pre-cast gels that "drop-in" to a standard gel tank, such as those provided by the Novex® brand of Invitrogen Corporation, or the ReadyAgarose® brand of Bio-Rad Laboratories. However, these gels still require "wet chemistry" handling procedures and remain time and labour intensive.

Other improvements include:
rigid gel plates into which the user can cast a gel matrix;
gel tanks that can simultaneously process multiple pre-cast or home made gels but which require much handling and wet chemistry preparation;
pre-cast gels that do not require a gel tank or buffers such as the "E-Gel™" system provided by Invitrogen Corporation (ref U.S. Pat. Nos. 5,582,702 and 5,865,924).

The "E-Gel™" system still incurs the inconvenience and handling overheads of manual sample loading and the use of a separate image capture station for analysis One of the commonest nucleic acid stainers employed during electrophoretic separation and imaging is ethidium bromide. This stainer has the disadvantage of requiring an Ultra-Violet (UV) light source to trigger the fluorescence upon which electrophoretic imaging relies. A requirement of UV imaging systems is to protect the user from UV radiation using either fully enclosed shielded light boxes or using goggles within a dark room.

An arrangement in common use is to use one of a number of commercially available gel imaging systems. A gel is processed in the traditional manner in a gel bath, but it is then manually transferred from the gel bath to the top surface of a separate light box contained within a light tight enclosure that contains a digital camera connected externally by cable to a viewer or an image printing device. Examples of available systems are manufactured by UVP Incorporated (brand name GelDoc-It), Bio-Rad Laboratories (brand name Gel Doc) or Synoptics Limited (brand name Syngene).

A similar solution is to use a walk-in dark room which hosts a UV light box and a camera. However, systems including these imaging techniques, still require significant levels of reagent preparation, careful manual sample loading and the set up and use of multiple pieces of apparatus.

Examples of systems which automate the traditional slab gel process are Helena Bio-Sciences, U.S. Pat. Nos. 4,954,237 and 5,147,522. These systems are relatively bulky and their automation process still involves the preparation, processing and automated handling of a traditional wet chemistry slab gel.

Fully automated electrophoresis devices that use capillary electrophoresis (as distinct from slab gel electrophoresis) address some of the issues involved in gel bath electrophoresis. However, these types of apparatus are large and expensive and require specially trained operators. They are normally used to carry out high resolution separation (down to a single base pair) of nucleic acids or high throughput single nucleotide polymorphism (SNP) analysis where automation is essential. An example of this type of system is the Applied Biosystems Inc Prism 3100 Genetic Analyser. The cost and complexity of these systems usually prohibits their use in small laboratories.

Microfluidic devices are beginning to be used in molecular biology. The Agilent Bio-analyser 2100 is a bench top device using the Caliper "Labchip®". This system exploits microfluidic techniques to achieve rapid separation. The system is however not fully automated and samples are processed in a serial (as opposed to parallel) fashion.

The challenges for systems that seek to replace slab gel electrophoresis and aim to achieve significant reductions in separation time are:
to eliminate the need for reagent preparation (gel, buffer, electrolyte) other than those associated with test sample preparation.

SUMMARY

In addition, a number of challenges exist in the general field of analysing biological and or biochemical samples such as:
to allow the user to load samples in a range of different standard laboratory vessel types;
to employ a micro-scale separation device to speed up molecule separation without the risk of joule heating;

to achieve highly parallel testing leading to improved sample throughput;

to reduce the quantities (therefore the cost) of reagents and test samples used;

to automate the process such that process steps are integrated and user intervention is minimised;

to achieve these improvements using a very small footprint;

to achieve all of the above in a manner which is cost competitive with traditional slab gel processing.

It is the object of the present invention to provide an analysis instrument in which the above challenges are addressed and whereby samples are analysed in a quick, clean and efficient manner.

In accordance with a first aspect of the present invention, there is provided an analysis instrument for processing a microfluidic device, comprising sample storage means, a microfluidic device holder, sample loading means for loading sample into a microfluidic device disposed in the holder, processing means for enabling a reaction in a microfluidic device, and detection means for detecting and/or measuring the reaction, characterised in that the microfluidic device holder is adapted to hold the microfluidic device comprising or including a tape in position for processing and/or detection.

The reaction carried out in the microfluidic device may be electro-chemical and/or bio-chemical.

Preferably, the sample loading means is moveable relative to the sample storage means and relative to the microfluidic device holder.

The instrument may further comprise opening means for opening a microfluidic device.

Preferably, the sample loading means and the microfluidic device opening means are disposed a fixed distance apart on a moveable common support and spaced such that the sample loading means can acquire sample from the sample storage means whilst at the same time the microfluidic device opening means opens the microfluidic device.

The sample loading means may comprise a nozzle, the nozzle being adapted to removably mount a pipette tip, the nozzle further being operably attached to a pump for pumping liquid into a mounted pipette tip.

Alternatively, the sample loading means comprises a pump, which can aspirate liquid from the sample storage means and dispense liquid into the microfluidic device. Preferably, the pump has a pump nozzle, the pump nozzle being attachable to a pipette tip.

Preferably the pump and the microfluidic device opening means are mounted to a common support structure and they are spaced a fixed distance apart such that the pump can acquire a new sample at the same time as the microfluidic device opening means prepares the microfluidic device for receiving that new sample.

Optionally the pump and the microfluidic device opening means are mounted to a common support structure and they are spaced a fixed distance apart such that the pump can pick up a pipette tip at the same time as the microfluidic device opening means prepares the microfluidic device for receiving that new sample.

The instrument may further include means for removal of a used pipette tip from the nozzle. The removal means may comprise a flange, the pipette tip being removed by relative movement between the mounted pipette tip and the flange. Preferably, the instrument includes a receptacle for receiving a spent pipette tip.

Preferably, the instrument includes a fresh pipette tip store adapted to store pipette tips such that the nozzle can be brought into contact with a pipette tip for attachment to the nozzle. In this embodiment, the receptacle and the store are preferably parts of a single demountable unit.

Preferably, the microfluidic device opening means comprises a piercing tool for penetrating a membrane of the microfluidic device. The piercing tool may be removably mounted on the moveable common support, and said piercing tool may comprise a needle.

Preferably, the needle has a shaped point that can cut an opening in the microfluidic device in the form of a flap that remains joined to the device.

The instrument may include means for removal of a used needle from the moveable common support.

Preferably, the removal means comprises a flange, the used needle being removed by relative movement between the needle and the flange. The instrument preferably includes a receptacle for receiving a used needle.

Preferably, the analysis instrument comprises an automatic needle changeover means, in the event that the needle becomes blunt through usage.

Preferably the needle comprises a means of automatic attachment to the automatic needle changeover means.

This enables rapid attachment and removal without the use of any tools and without the need for user intervention.

Preferably, the automatic needle changeover means comprises a cartridge containing a receptacle to receive the used needle and a receptacle containing a new needle.

Preferably, the cartridge is automatically loadable into the automatic needle changeover means in the instrument. This eliminates a hazard as a user prevented from handling both the old and the new needles.

Preferably the cartridge can be automatically drawn into the analysis instrument under the control of machine software.

Preferably a needle attachment means, the needle cartridge and the motion system of the analysis instrument can cooperate to achieve automated needle changeover.

Preferably, the instrument is adapted to maintain a count of needle usage to alert a user to a requirement for needle changeover.

Preferably this process is aided by the instrument control software which will maintain a count of needle usage (number of piercings) such that the external personal computer can alert the user to a requirement for needle changeover. Accordingly, the potential disadvantage of the needle becoming blunt is overcome.

The instrument may include a fresh needle store adapted to store needles such that the common support can be brought into contact with a needle for attachment thereto. Preferably, the receptacle and the store are parts of a single demountable unit.

Preferably, the sample storage means comprises a sample holder, which can accommodate one or more standard laboratory vials or a standard laboratory multi-well plate.

The instrument may be operable to process a single sample using one single element of a microfluidic device.

Alternatively, the instrument may be operable to process a single sample using one single element of a microfluidic device by comprising a single sample loading means only, the single sample loading means being enabled to load sample one sample at a time from a plurality of sample holders, and deliver each said sample to a separate element of a microfluidic device.

Preferably, the instrument is operable to permit a batch of multiple samples to be processed up to the limit of the test element capacity of a single microfluidic device.

Alternatively, the instrument is operable to permit a batch of multiple samples to be processed up to the limit of the capacity of a microfluidic device feeder module.

Thus, the system has the flexibility to cope with a range of samples from one to many.

Preferably, the sample storage means includes a pipette tip holder, which may be a used pipette tip holder.

Preferably the pump includes means for removably attaching a pipette tip to the pump.

The pump must be configured to pick up a pipette tip for one time use in the handling of a sample. In addition, the pump can dispose of a used pipette tip once the sample is loaded into the microfluidic device.

Preferably, the used pipette tip holder is provided with removal means for removing the pipette tip from the pump.

Preferably, the removal means is provided with an opening shaped to catch a used pipette tip so that it is retained in the used pipette tip holder when the pump is retracted.

Preferably, the sample loading means is moveable to ensure the used pipette tip is caught upon the opening of the used pipette holder.

Optionally, the sample storage means is mounted on a platform, moveable relative to the sample detection means.

Preferably, the sample detection means and the microfluidic device holder are moveable relative to one another to allow samples within the microfluidic device to be positioned at a predetermined location for detection.

Preferably, the microfluidic device holder is adapted to accommodate a microfluidic device having a plurality of microfluidic processing elements such that each said element can be individually detected by the detection means.

Preferably, the microfluidic device holder is mounted on the same platform as the sample storage means.

Preferably, the microfluidic device holder has one or more aperture to allow the reaction in the sample to be monitored.

Optionally, the sample processing equipment holder is provided with a reflective surface adjacent to the position in which microfluidic processing apparatus is mountable.

Preferably, the processing means is adapted to facilitate bio-molecular separation.

Preferably, the sample processing means comprises probes for applying voltages to a sample, the probes being configured in an array to correspond with an equivalent array of conductive pads on the microfluidic device.

Preferably, the electrical polarity of the probes is controllable.

Optionally, the processing means can comprise any combination of
sample preparation including fractionation, isolation or purification
polymerase chain reaction
bio-molecular separation
molecular binding by affinity
isolation of any reaction end products
retrieval of any reaction end products.

Optionally, the microfluidic device within the microfluidic device holder can be indexed past a fixed detection point so that one or more test elements can be monitored for the results of any reaction process. Test elements may be monitored simultaneously.

Preferably, the sample loading means is mounted on a frame above the sample storage means for movement to and from the sample storage means and in a direction substantially perpendicular to the movement direction of the sample storage means.

Optionally, the sample processing means comprises a plurality of probes for applying voltage to a sample in a microfluidic device mounted in the holder. The probes may be disposed to contact conductive pads of the microfluidic device. The instrument may be adapted to enable electrophoretic separation of a sample containing, molecules of DNA or RNA or proteins.

Optionally, the instrument may be adapted to enable electro-kinetic transport of a biological sample past a zone within the microfluidic device that contains one or more antibodies, such that binding between the sample and any antibody material can be enabled.

Preferably, the detection means is adapted to detect change in conductivity in a sample.

Optionally, the detection means can be electro-chemical, whose function is enabled by electrical probes in contact with the microfluidic device such that any change in conductivity from a sample reaction process can be detected.

Preferably, the sample detection means comprises an optical assembly.

Preferably, the optical assembly includes a light source for exciting a sample in a microfluidic device holder and a receiver arranged to receive a signal from said microfluidic device holder, the receiver being arranged in an optical path relative to the microfluidic device holder.

Preferably, the optical assembly includes a light source capable of emitting at a predetermined first frequency for excitation of constituents of the sample to allow the sample to emit light at a second frequency, and a light receiver. The receiver may comprise a charged coupled device, or a line scan camera. The receiver may be configured to send image data to an external data processing device.

Preferably, the receiver comprises a charged coupled device.

Alternatively, the receiver is a line scan camera.

Preferably, the light source and receiver are on the same side of the Microfluidic device holder.

Optionally, the light source and receiver are on opposing sides of the microfluidic device holder.

Optionally, the light source projects directly into the light path of the optical assembly.

Optionally, the light source emits in the ultra-violet range of the electromagnetic spectrum.

Preferably, the receiver is capable of detecting light in the visible range of the electromagnetic spectrum.

Preferably, the receiver can be configured to send image data to an external data processing device.

Preferably, the data processing device is a Personal Computer.

Optionally, the data processing device, which may be a Personal Computer, can be embodied within the analysis instrument.

Preferably, the system control of the analysis instrument is hosted on that same personal computer.

The instrument may include an on-board system controller, the controller being programmable by a user to perform automated microfluidic device processing, or, as an alternative, the instrument may be adapted to be controlled by an external system controller.

Preferably, the analysis instrument is configured to operate from low voltage electrical supplies and that an external dc power supply, such as is used by a laptop computer, can be its primary source of electrical supply.

The system can be modularly extended to incorporate automated handling of multiple microfluidic devices, for example, to allow continuous processing of a micro-titre plate and/or automated handling of pipette tips and/or automated handling and storage of used microfluidic devices.

Preferably, the automated handling is provided by a feeder module removeably attachable to the analysis instrument and that this module can store multiple microfluidic devices that can be automatically loaded into or unloaded from the microfluidic device holder.

One benefit of the invention described herein over the current state of the art is that it integrates a novel microfluidic device with a novel analysis instrument possessing an adaptable handling configuration. The resulting system is very easy to use and can achieve high test throughput within an extremely small footprint.

The sample loading mechanism can use a consumable laboratory pipette tip which eliminates the risk of contamination from previously processed samples, includes a means of storing and disposing of tips, and optionally allows the sample loading pipette to be washed at a wash station within the apparatus.

The instrument may include a feeder module removeably attachable to the instrument and storing multiple microfluidic devices for automatic loading into or unloading from the microfluidic device holder.

The sample loading mechanism can use a consumable laboratory pipette tip which eliminates the risk of contamination from previously processed samples, includes a means of storing and disposing of tips, and optionally allows the sample loading pipette to be washed at a wash station within the apparatus.

In accordance with a second aspect of the invention there is provided a microfluidic processing device, comprising a reaction chamber, a sample loading chamber into which a sample is injectable, the reaction chamber being operatively connected to the sample loading chamber, a cover that extends across at least part of the sample loading chamber, the cover and the reaction chamber comprising pierceable material and being separated by an overspill cavity configured to accept any overspill of an injected sample.

Preferably, the reaction chamber contains a molecular separation medium.

The reaction chamber may be a channel and the microfluidic processing device may further include a receiving chamber at an end of the reaction channel remote from the sample loading chamber.

The microfluidic device may be used with the analysis instrument of the first aspect of the invention.

The presence of the overspill cavity allows excess reagent that would otherwise be spilled into the analysis instrument to be contained between the cover and the loading chamber.

Preferably, the cover and/or the loading chamber are manufactured from polymer film.

Preferably, the microfluidic processing device further comprises electrodes.

The chambers and electrodes of a single microfluidic element combine to become a single processing element. Preferably, a single processing element is provided with three electrical contacts.

Preferably, the three electrical contacts operate as a cathode, a compacting electrode and an anode.

Preferably, the cathode is arranged in the loading chamber, the compacting electrode is arranged at the upper end of the reaction channel and the anode in the receiving chamber.

The polarities of the electrical contacts may be reversed.

Preferably, the electrical contacts extend from a position outside the microfluidic device to a position inside the microfluidic device.

Preferably, the electrical contacts have coupling means for connecting them to an external electrical supply to allow the creation of a circuit incorporating the reaction chamber.

Preferably, reagents within the microfluidic device are pre-filled at the point of manufacture, thereby avoiding the need for reagent handling at the point of use.

Preferably, the loading chamber is pre-filled with an electrolyte.

Preferably, the reaction channel is pre-filled with a molecular separation medium.

Preferably, the receiving pocket is pre-filled with either the molecular separation medium or an electrolytic buffer.

The microfluidic processing device may have a laminated structure.

Preferably, the microfluidic processing device includes optical fiducial marks whose position is known relative to the reaction chamber and which can be acquired by the detection means of an analysis instrument to accurately identify the position of a reaction process. microfluidic device holder.

Preferably the device further comprises an identifying label or tab.

Preferably this tab can be used as a handling tab for loading and unloading the microfluidic device such that manual contact with any optical surface of the device is avoided.

According to a third aspect of the invention there is provided a kit comprising an instrument as hereinbefore defined, and a microfluidic device as herein defined.

One benefit of the invention described herein over the current state of the art is that it integrates a novel microfluidic device with a novel analysis instrument possessing an adaptable handling configuration. The resulting system is very easy to use and can achieve high test throughput within an extremely small footprint.

BRIEF DESCRIPTION OF THE DRAWINGS

The present invention will now be described by way of example only with reference to the accompanying drawings in which:

FIGS. 4a to 4G show the automated handling sequence for a test sample;

FIGS. 6a and 6b show an arrangement for retaining the pipette tip holder within the instrument;

FIGS. 6c and 6d show the use of the same arrangement as in FIGS. 6a and 6b to retain a needle cartridge whereby the piercing tool for the microfluidic device can be automatically replaced;

DETAILED DESCRIPTION

Figure 1:
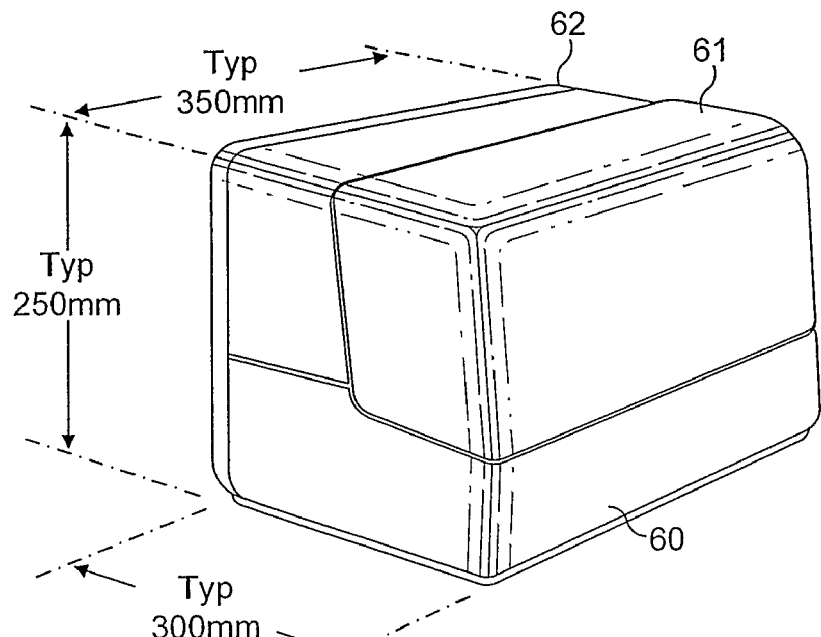
FIG. 1 shows a general external view of the processing instrument for a microfluidic device.

FIG. 1 shows a typical instrument enclosure. A main enclosure component 60 carries a lid 61 at the front for operator access to the loading and unloading stations and a rear cover 62 for access to the onboard drive and control circuit boards.

Figure 2:
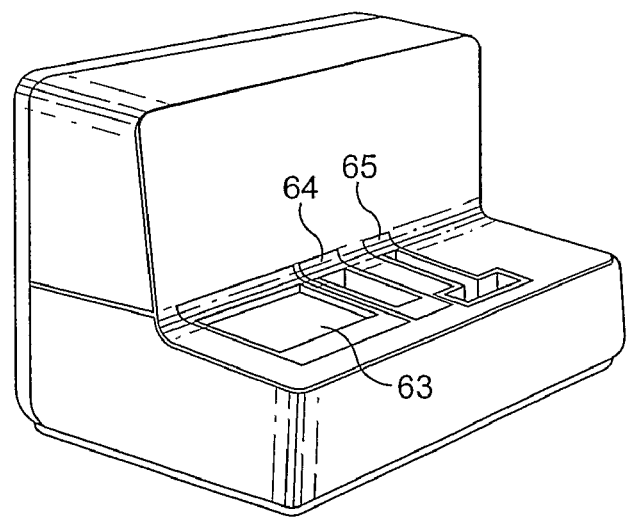
FIG. 2 shows the zones of the instrument that an operator will access for loading the system.

FIG. 2 shows the operator loading stations. Station 63 is the sample loading and unloading station, station 64 is the pipette tip loading and unloading station, station 65 is the microfluidic device loading and unloading station.

Figure 3A:
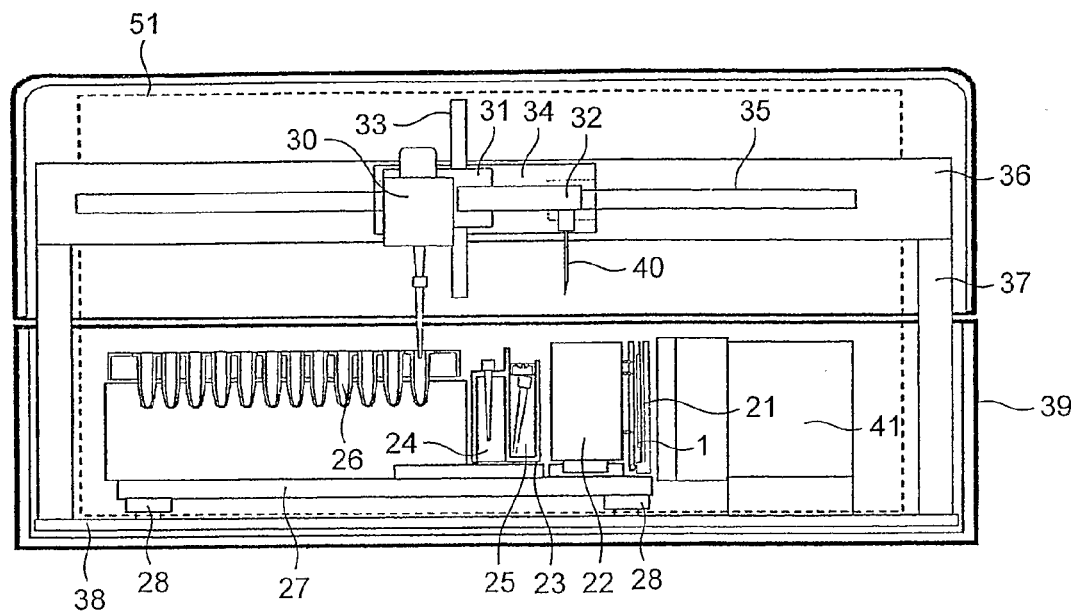
FIG. 3a is a side view of an embodiment of the present invention and FIG. 3b is a corresponding plan view.
Figure 3B:
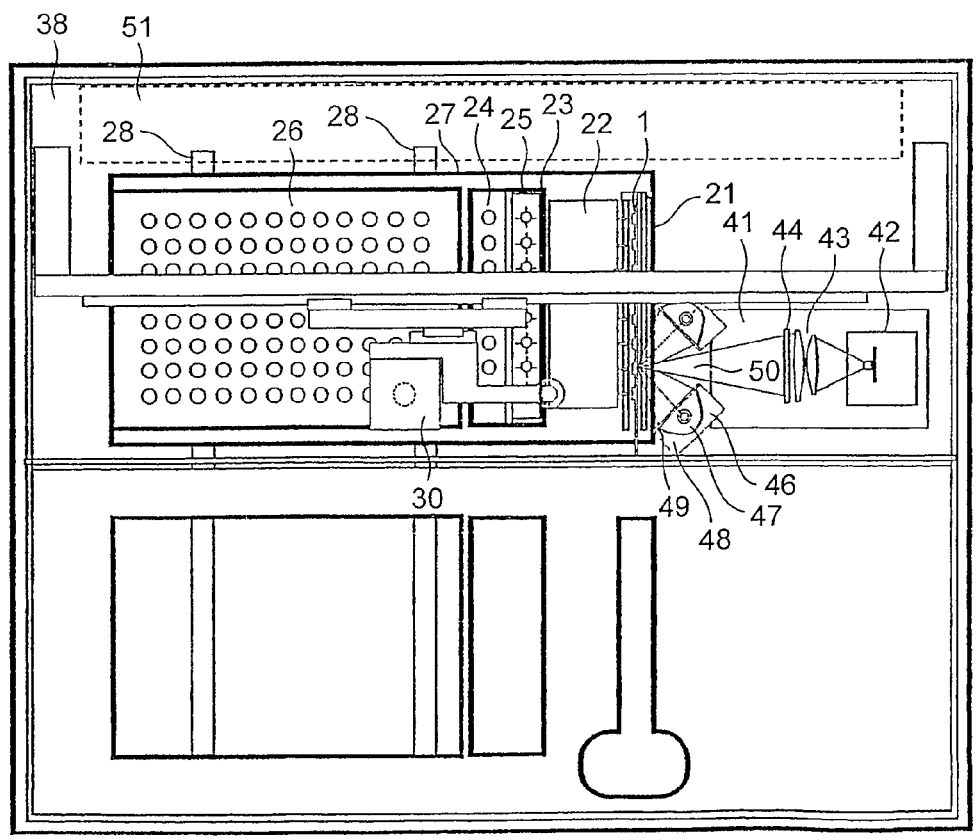

FIGS. 3a and 3b show a microfluidic device 1 held within holder 21 which is mounted to platform 27 which is movable in one axis along slides 28. These slides are attached to baseplate 38. Also mounted to platform 27 is the electrical probe block assembly 22, a pipette tip holder 23 which can store unused pipette tips 24 and used pipette tips 25. A suitable pipette tip is, for example, the "Eppendorf PMP-885-501W" and a typical sample loading volume is around 1 microlitre, but conveniently could be in the range 0.1 to 5 mcrolitres. Also mounted on this platform is the test sample storage device, in this case a 96 well micro-titer plate 26. Nothing precludes other types of micro-titer plate (e.g. 384 well) or even the use of individual vials for sample storage.

Above the movable platform 27 is a fixed gantry beam 36 supported by pillars 37 on the baseplate 38. Baseplate 38, in turn, is attached to lower casing 39. A slide 35, along which a carriage plate 34 can move is attached to the gantry 36. This movement is transverse to the movement of platform 27.

A vertical slide 33 along which carriage plate 31 can move is attached to carriage plate 34. A pump 30 and an arm 32 which locates a piercing tool 40 is attached to carriage plate 31.

Baseplate 38 also supports the image capture assembly 41 which comprises a CCD camera 42, a lens 43, a filter 44, a mirror (or prism) 45, a lampholder 46 which contains lamp tubes 47, reflectors 48, lenses 49 and a slit 50 through which the camera light path can pass.

Control for the various active functions of the instrument and delivery of the captured images is provided by electronic controller 51, which comprises a micro-controller whose programme sequence is delivered from an external personal computer via, for example, a USB cable. The particular architecture allows the instrument enclosure to be serviced by only two cables, one for delivery of DC power, the other a communications cable to the external PC. This layout contributes to the extremely compact footprint of the instrument enclosure.

FIGS. 3a and 3b also show the pump 30 positioned ready to withdraw test sample from the first well of the second row of the micro-titer plate 26. This is achieved by suitably synchronizing the positions of platform 27, carriage 34 and carriage 31 which are controlled as elements of a 3-axis Cartesian robot. The drives and controls for this X, Y, Z system are not described since the means of achieving this are already known, but, for example, the drives can be lead screws driven by stepper motors and the control can be from a software sequence embedded in a micro-controller.

FIGS. 4a to 4g show a "snapshot" of the processing sequence whereby platform 27 has moved from the operator load station 51 into the sample transfer station. This station is behind bulkhead 52 so that load station 51 is isolated from the internal mechanisms of the instrument.

An advantageous step in this sequence is that the piercing tool 40 opens an access port in the microfluidic device 1 by means of penetration of pocket 7 and cavity 11 and that it does this simultaneously with the pick up of pipette tip 24.

Figure 5A:
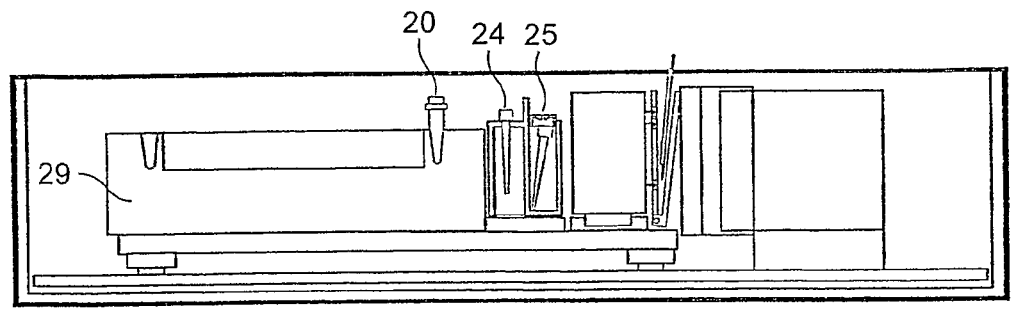
FIG. 5a shows how test samples can be loaded from open topped laboratory vials.
Figure 5B:
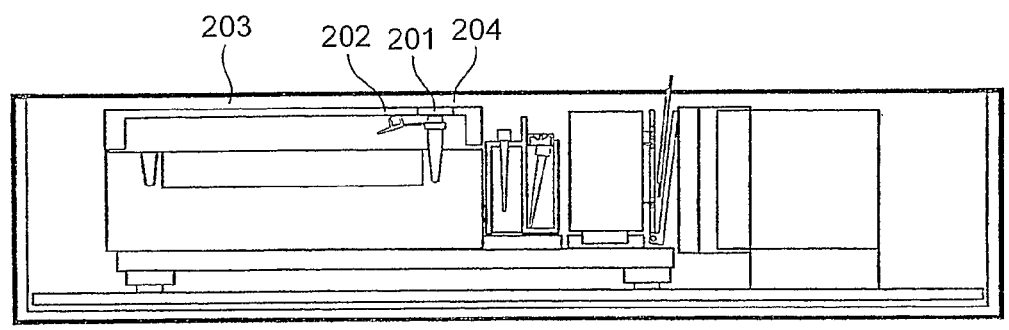
FIG. 5b shows how test samples can be loaded from laboratory vials with a hinged lid.
Figure 5C:
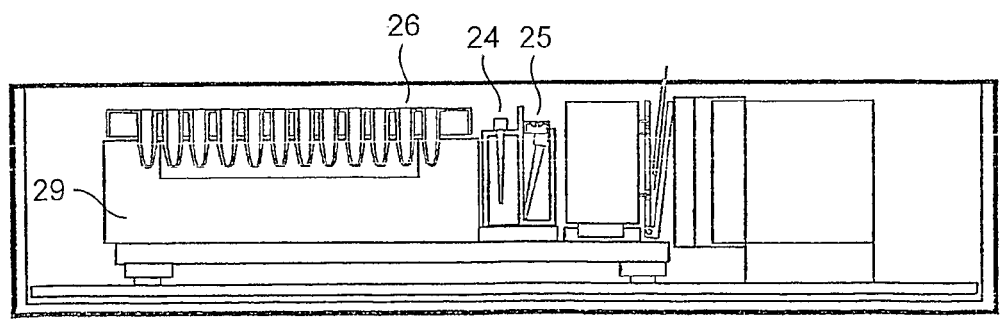
FIG. 5c shows how test samples can be loaded from a multi well plate.

FIGS. 5a to 5c show arrangements that allow the user to load test samples either in individual vials 20 or in a strip of vials (for example, a PCR strip) or in a multi-well plate 26, which can be a 96 well micro-titre plate or a 96 well PCR thermo-cycler plate. These vials and plates are mounted on a common support block 29. This arrangement is also compatible with other types of micro-titre plate, for example, a 384 well plate. FIG. 5b shows the use of a vial 201 with hinged lid 202. The lid is trapped under the lid retaining plate 203, that has an access aperture 204.

FIG. 6a shows an arrangement that allows pipette tips 24 to be loaded in a removable pipette tip holder 23 which can be securely retained within support block 160 by a latch mechanism 161 which engages the tongue 162 of a pivotable lever 163 into an undercut feature 164 on the underside of pipette tip holder 23. The pipette tip holder 23 incorporates a slotted flange 165 which allows a used tip to be entered into the pipette tip holder 23 such that a small sideways motion of the pipette tip 25 engages the pipette tip with the underside of the slotted flange 165 and such that when the pump nozzle holding the pipette tip is retracted vertically upwards, the used pipette tip is disengaged to fall into the pipette tip holder. The latch mechanism 161 ensures that the pipette tip holder 23 is not withdrawn during this operation. FIG. 6b shows the latch mechanism 161 disengaged to allow the operator to remove and replace the pipette tip holder in the direction of arrow "A".

FIG. 6c shows how this same arrangement can be used to allow automated replacement of the piercing tool for the microfluidic device, this piercing tool comprising a needle 167. A needle cartridge 166 (instead of the pipette tip holder 23) contains a new needle 167 and space to accommodate the used needle 168. The cartridge may have a peel-off or removable lid to expose the new needle. The new needle can be retained temporarily during the loading process by a foam plug 170. Needle replacement involves a motion sequence of the needle holder 169 which is mounted on, for example, arm 32 of FIG. 3a. With further reference to FIG. 3a it can be seen that the motion system capable of manipulating pump 30 is equally capable of manipulating needle 167 as part of an automated replacement sequence. With reference to FIG. 6d, the needle holder 169 enters the used needle 168 into a cavity of the needle cartridge 166 which incorporates a similar slotted flange 165 to that used in pipette tip holder 23, thereby enabling removal of the used needle. The needle holder 166 is prevented from withdrawal by the retaining action of latch mechanism 161. Thus the holder 160 and latch mechanism 161 can serve an important dual function, that is, retention of a pipette tip holder during normal use or retention of a needle cartridge during the maintenance sequence for replacing the piercing tool. The needle replacement sequence can be initiated by the system storing a count of the number of piercings carried out (for example in EEPROM) and alerting the operator on the system PC once a preset count is reached.

Figure 7:
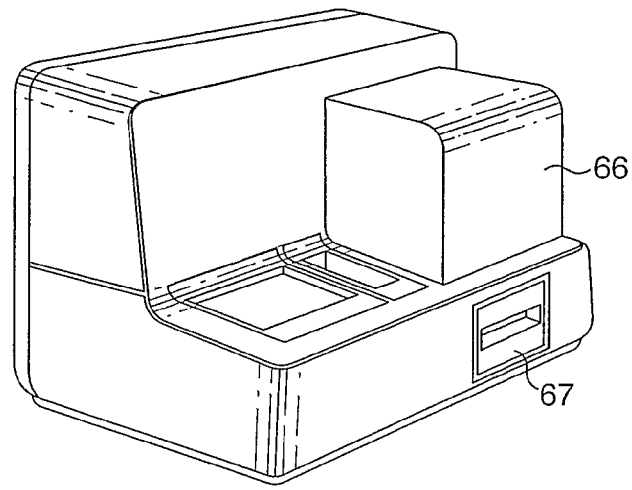
FIG. 7 shows the instrument enclosure configured to accommodate an automatic feeder module for microfluidic devices.

FIG. 7 shows the integration of a separate discrete feeder module 66 whose function is to allow multiple microfluidic devices to be automatically loaded and discarded. Used microfluidic devices are disposed of into a drawer 67 which can be opened for emptying. This configuration is targeted at providing "hands off" operation for automated processing of one complete multi-well plate of test samples.

Figure 8:
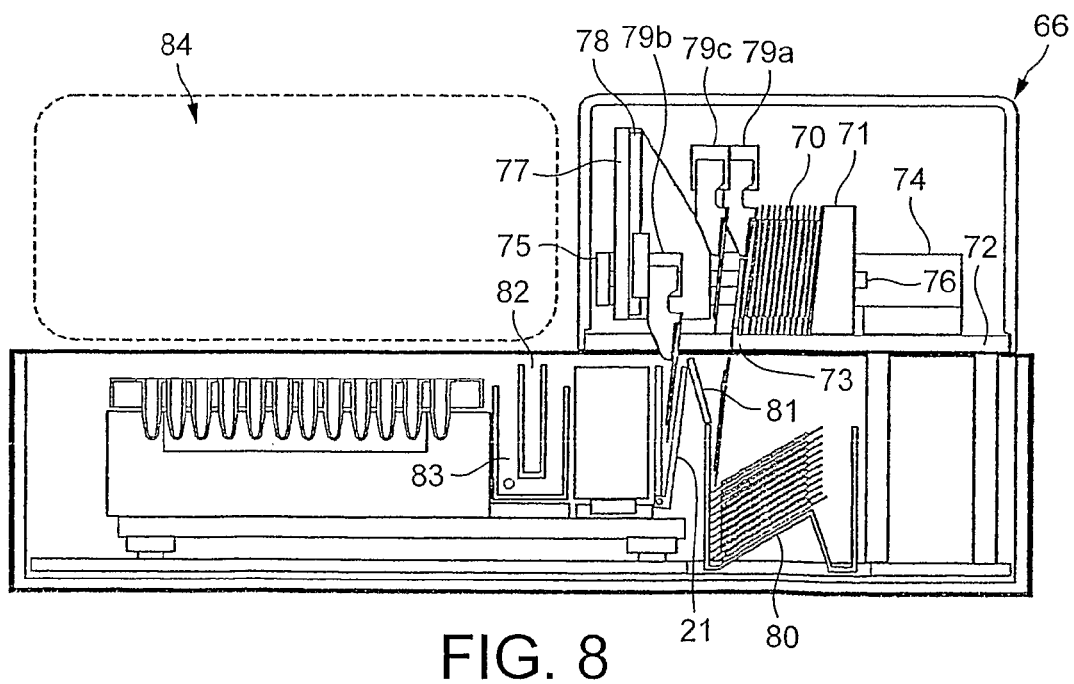
FIG. 8 shows a more detailed side view of the feeder module configuration.

FIG. 8 shows details of the feeder mechanism. A loading hopper 70 can stack multiple microfluidic devices 1. These devices are held together by a spring loaded paddle 71 which pushes the stack of microfluidic devices 1 against a restraining lip 73 which extends up each side and along the bottom edge of the microfluidic device at the front of the stack. Paddle 71 mounts to a slide which is attached to support plate 72. Surrounding the hopper area is a frame comprising side plates 74 and a cross plate 75. This frame is attached to support plate 72. The side plates 74 incorporate slides 76 which carry a cross beam 77 which carries a vertical slide 78 to which is mounted a pick up tool 79. This tool can be positioned by means of suitable linear actuator drives (not shown) such that at position 79a it can pick a microfluidic device from the front of the hopper stack 70, at position 79b it can load the microfluidic device into the holder 21, at position 79c it can deposit the used tape into the waste trap 80 which is integrated with drawer 67.

The remaining requirement for fully automated handling is to provide automated pipette tip handling. This can be accomplished by the pick and place unit 84 which will load pipette tips from a standard pipette holding tray into the tip holder 23.

The alternative is to replace tip holder 23 with a wash bath 82. The liquid transfer pump 30 will be fed with a wash compound and pump fresh washing agent through the liquid transfer nozzle into wash bath 82 which will overspill into catchment tray 83, which will drain into a sump container underneath the test sample loading zone.

Figure 9:
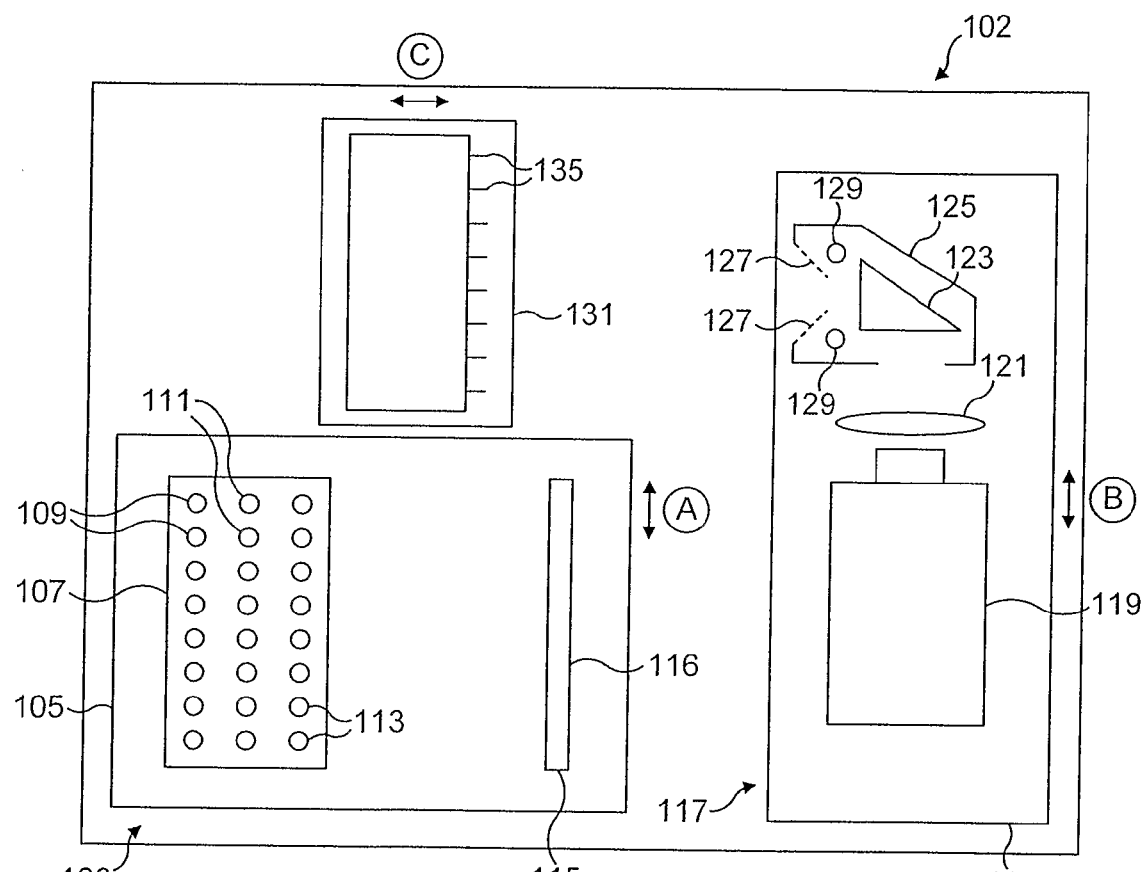
FIG. 9 is a plan view of the base section of an alternative embodiment of an analysis instrument in accordance with the present invention.

FIG. 9, shows an alternative embodiment of the analysis instrument of the present invention. The base area 102 of the analysis instrument is shown in plan and comprises a sample assembly 103 having a sample assembly platform 105 upon which a cartridge holder 107 and a tape holder 115 are mounted. The cartridge holder 107 contains a pipette tip holder 109, a used pipette tip holder 111 and a sample chamber 113. The sample to be analysed is kept in chamber 113 and the pipette tips are kept in pipette tip holder 109 prior to their use.

Figure 10:
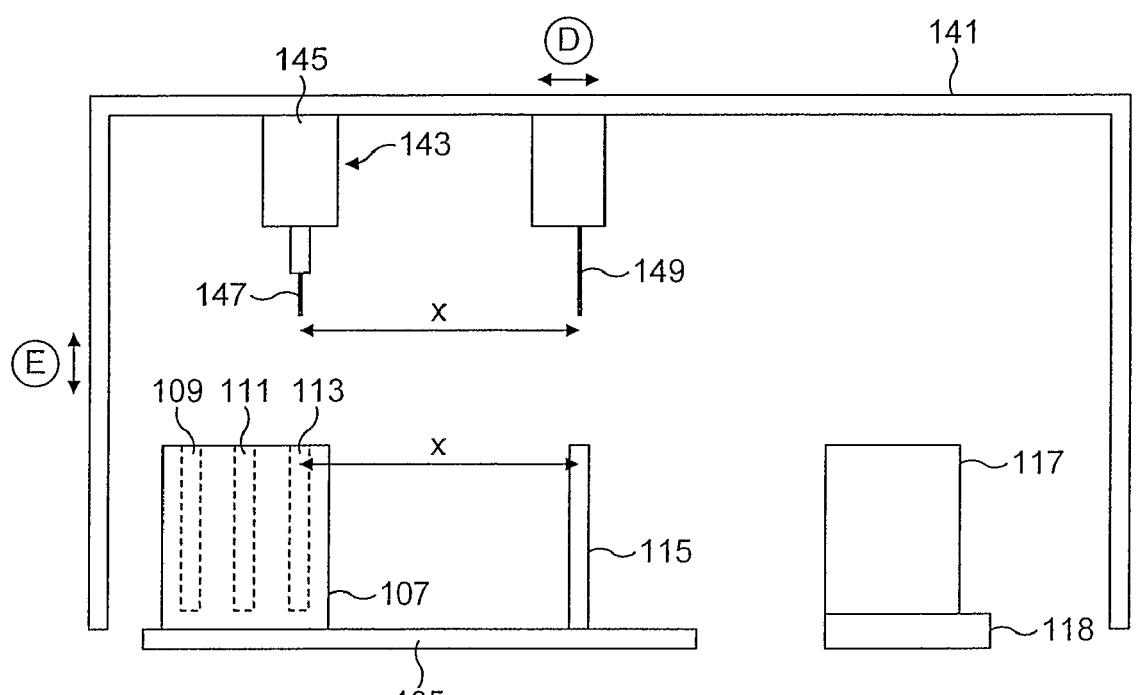
FIG. 10 is a side view of the analysis instrument of FIG. 9.

The used pipette tip holder 111 has a keyed shape. That is, the entrance to the pipette tip holder is narrowed towards one end of it. This narrowing allows the edge of a pipette tip to be caught on the narrowed section of the used pipette tip holder and assists in the removal of the pipette tip from the pump nozzle 147 (FIG. 10). It should be noted that the cartridge holder 107 accommodates eight pipette tip holders 109, used pipette tip holders 111 and sample chambers 113. This size of cartridge holder 107 has been chosen for convenience and it is anticipated that a cartridge holder with space for more than or less than eight samples could be used.

The tape holder 115 consists of a box shaped section having one open side 157 (FIG. 13) and an open top end 116 into which a microfluidic processing apparatus can be inserted.

The analysis instrument is designed such that each of the microfluidic processing channels is substantially in alignment with the corresponding sample chamber 113. Consequently, the microfluidic processing tape as used with this embodiment of the present invention will contain eight separate microfluidic processing areas. Platform 5 is mounted on rails that allow it to move to and from the position of the probe block 133.

The optical assembly 117 consists of a platform 118 which allows the entire assembly to move in direction B. A camera 119 is provided with a lens 121 and a prism 123 which is used to redirect a beam of light that has been reflected from the sample when in use. The prism is partially enclosed within an opaque enclosure 125 which also partially encloses two radiation sources 129. In this example, these sources emit ultra-violet radiation at a wavelength of approximately 310 nm. It will be appreciated that, depending upon the analysis undertaken, radiation sources emitting radiation at other wavelengths may be used. The radiation sources are provided with a transparent screen 127 that allows radiation to pass out from the opaque enclosure 125 towards the probe block 131 where analysis of the sample is undertaken.

The probe block 131 is this example contains a number of pins 135. As can be seen from FIG. 15, these pins are arranged such that two pins in each row are positioned towards the top of the probe block and a single pin is positioned towards the bottom. The polarity of each of the pins may be change to enhance analysis of the sample.

FIG. 10 shows the side view of the embodiment of the analysis instrument of FIG. 9. In this diagram the optical assembly 117, the cartridge holder 107 and the tape holder 115 are shown as described above.

In addition, a sample transfer means is shown. The sample transfer means consists of a tape filler having a pump 145, connected to a pump nozzle 147 that extends downwards towards the position of the cartridge holder 107. The sample transfer means is further provided with a tape puncturing means 149 which in this example comprises a needle with a shaped point that extends down towards the position of the tape holder 115.

These devices are mounted on a moveable frame 41 which allows movement in directions D and E as shown in FIG. 10. In addition, the distance between the pump nozzle 147 and the tape puncturing means 149 is defined by x. This distance is substantially identical to the distance between the tape holder 115 and the sample chamber 113, also denoted by X on FIG. 10.

Figure 13:
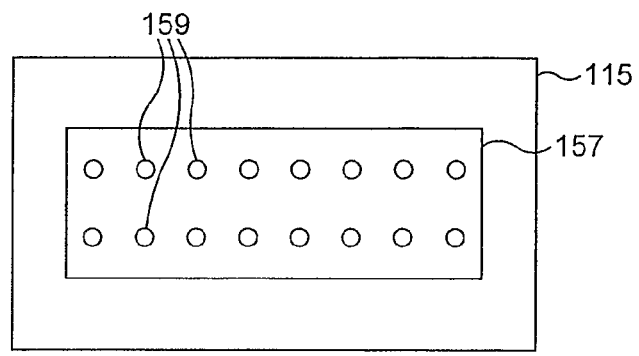
FIG. 13 is a side view of the microfluidic device holder of the embodiment of the present invention shown in FIGS. 9 and 10.
Figure 14:
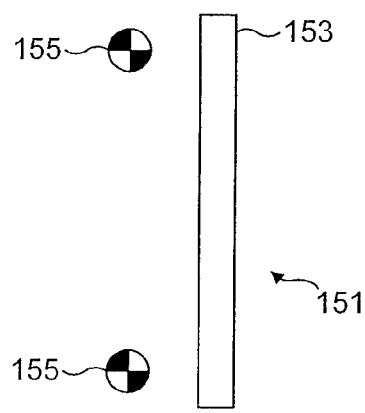
FIG. 14 shows quadrant markers and areas of interest found on the microfluidic processing apparatus used in the analysis instrument of the present invention.

FIG. 13 shows the side view of tape holder 115 and shows a number of reflective pads 159. In use, these pads provide a reflective background which lies behind the position of quadrant markers 155 which are found on a microfluidic processing device as shown in FIG. 14.

The combination of these reflective pads and the quadrant markers allows easy alignment of the optical assembly 117 to maximise the amount of reflected radiation that is detected by the camera 119.

In use a set of samples is loaded into the sample chambers 113 and a set of pipette tips are loaded into the pipette tip holders 109. A microfluidic processing device such as a microfluidic processing tape, having eight microfluidic processing areas is then loaded into the tape holder 115. Thereafter, the moveable frame 141 moves the tape filler 143 into position above the pipette tip holder 109 and is then lowered in order to pick up a pipette.

Thereafter, the tape filler moves to the position above the sample chamber 113 and is then lowered into a sample chamber 113 where the pump is actuated and the sample is drawn into a pipette which is coupled to the pump nozzle 147 of tape filler 143. Substantially simultaneously, the tape puncturing means 149 is lowered to the tape holder 115 where the tape puncturing means punctures a hole in a microfluidic processing area of the microfluidic processor (which in this example is in tape form).

Advantageously, therefore, a single processing step allows a hole to be punctured in the microfluidic processor and allows a pipette to be filled.

Thereafter, the pipette on the end of the pump nozzle 47 is moved to a position above the tape holder 15 and subsequently lowered to allow the microfluidic processing area to be filled with the sample.

These process steps are repeated until the samples have been removed from each of the sample chambers 13 and added to the corresponding microfluidic processing areas found in the tape holder 15.

Turning to FIG. 9, once the sample is in the microfluidic processing area 115, the sample assembly platform is moved in direction A towards the probe block 131 and the probe block 131 moves towards the tape holder. The probe block pins move through the open side 157 of the tape holder and are coupled to electrical connections upon the microfluidic processing areas.

Figure 15:
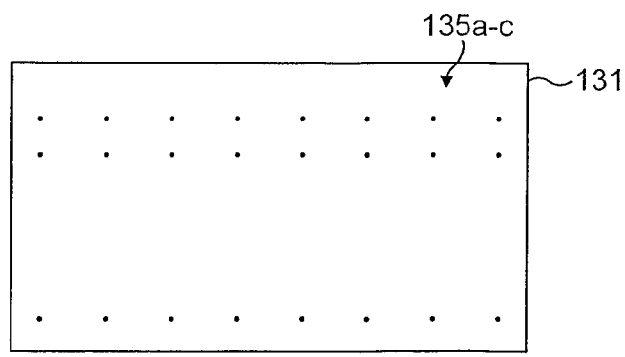
FIG. 15 is a side view of a probe block as used in the embodiment of FIGS. 9 and 10 of the present invention.

As can be seen in FIG. 15, there are sets of three pins which are coupled to each microfluidic processing area. The polarity of these pins can be reversed. For example, in the analysis of DNA, once the negatively charged DNA sample has been added to the microfluidic processing area, the polarity of pin 135a is set to negative and the polarity of pin 135b is set to positive. This allows the DNA to form a consistent mass at or near the electrode 135b. Thereafter, this electrode is switched off and electrode 135c is given a positive polarity so that the DNA sample can migrate down the column.

During this processing, the radiation sources 129 emit radiation at 310 nm onto the sample. In the case of a DNA sample such incident radiation provides an output at 600 nm in the visible spectrum. This radiation is provided to the camera by the total internal reflection by the prism 23 and the camera detects the lights and provides results accordingly.

Figure 11:
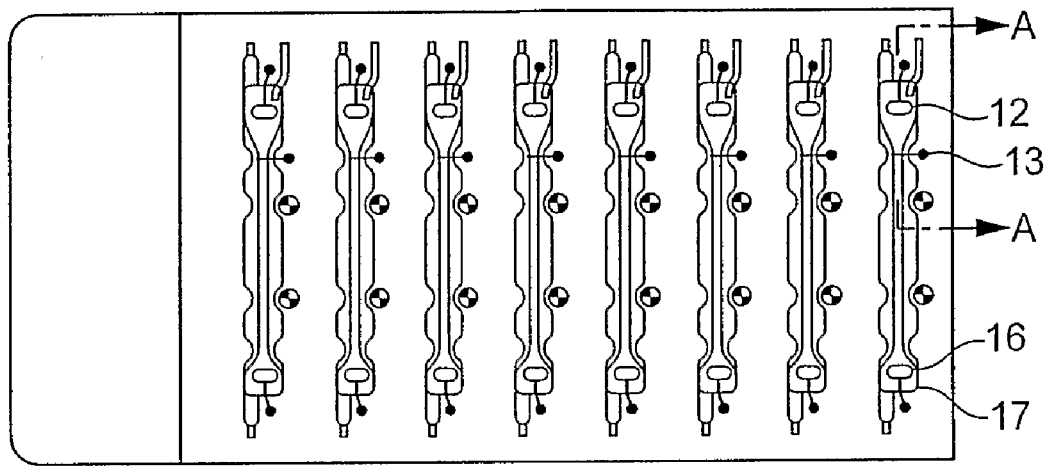
FIG. 11 is a plan view of a microfluidic processing device with eight separate microfluidic processing areas.
Figure 12:
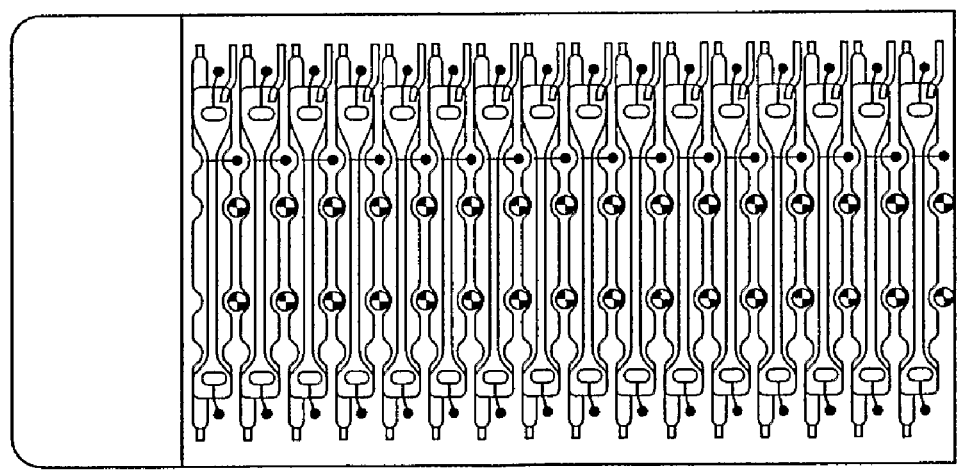
FIG. 12 is a plan view of a microfluidic processing device with sixteen separate microfluidic processing areas.

FIGS. 11 and 12 show the outline profile of a microfluidic device whose configuration is compatible with the instrument processing methods already described. The spacing between test elements on the microfluidic device is conveniently set at the same spacing as the wells of standard laboratory micro titre plates, for example, in FIG. 11 showing an 8-way microfluidic device, the spacing between elements is 9 mm to correspond with a 96 well plate. Similarly in FIG. 12 showing a 16-way microfluidic device, the spacing between elements is 4.5 mm to correspond with a 384 well plate. FIG. 11 also shows locations 12, 13 and 16 which are electrodes in contact with the reagents inside the device but which pass between layers of the device such they can be accessed by external probes 18 of FIG. 18.

Figure 16:
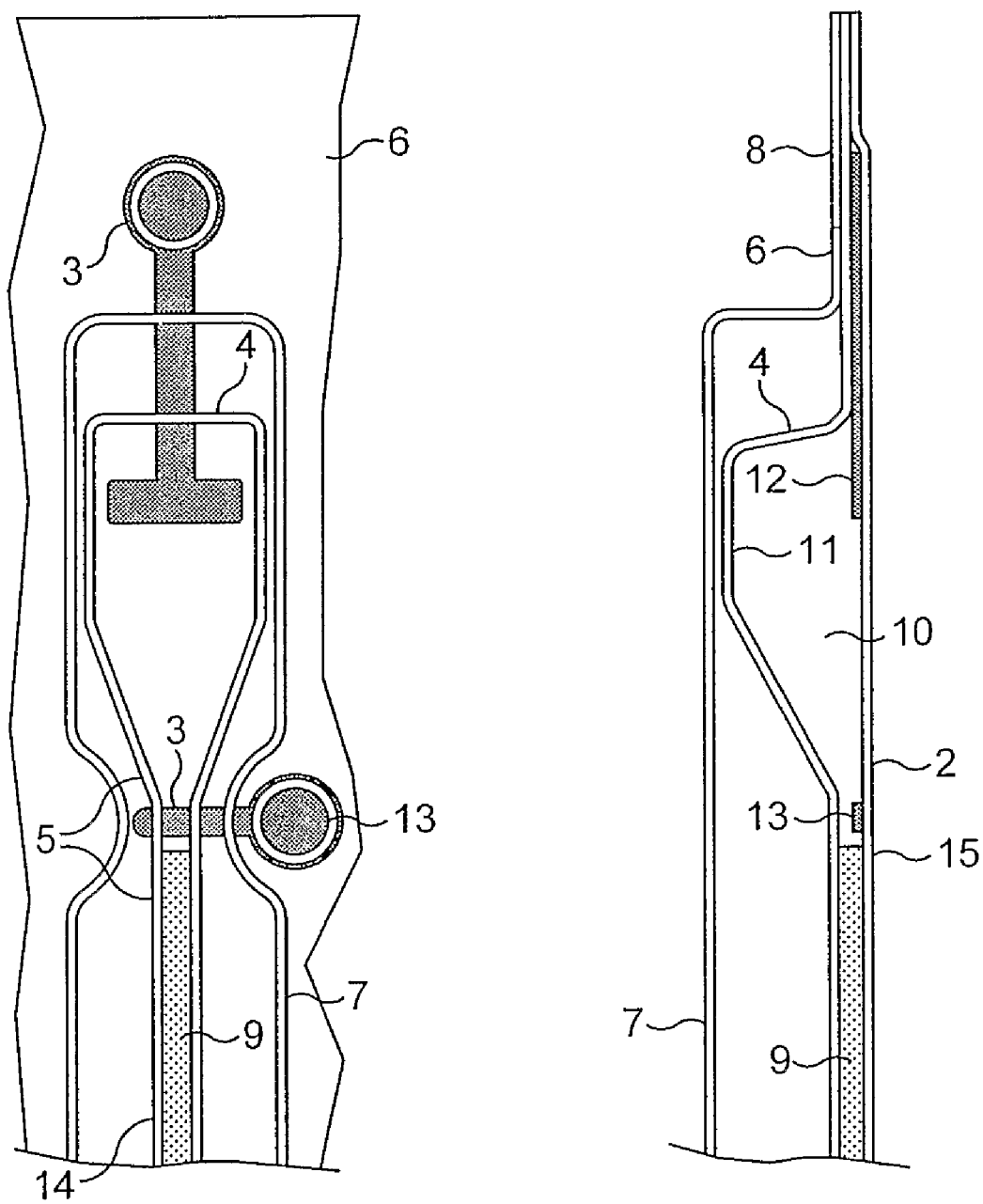
FIG. 16 shows details of the upper part of a single test element of the microfluidic device in accordance with the second aspect of the invention.
Figure 17A:
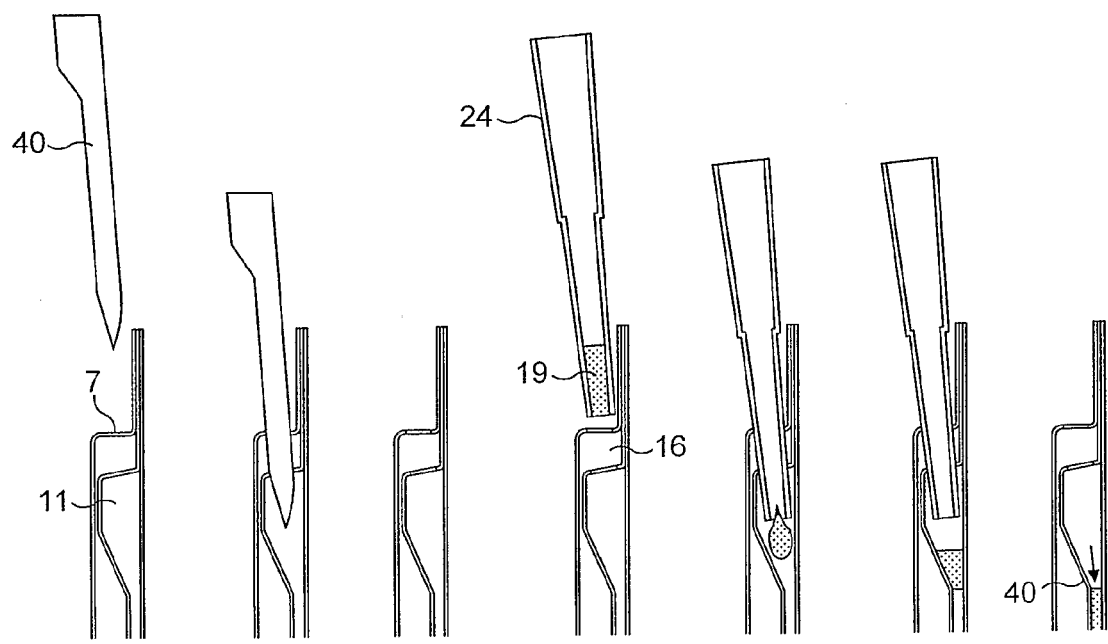
FIG. 17a shows how the microfluidic device is loaded with a test sample.
Figure 17B:
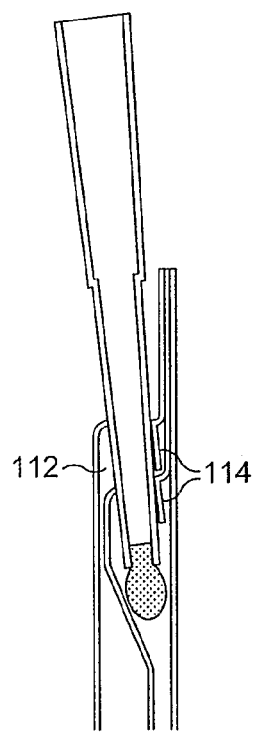
FIG. 17b shows further detail of the method of piercing the microfluidic device and the method of containment of any spillage.
Figure 18:
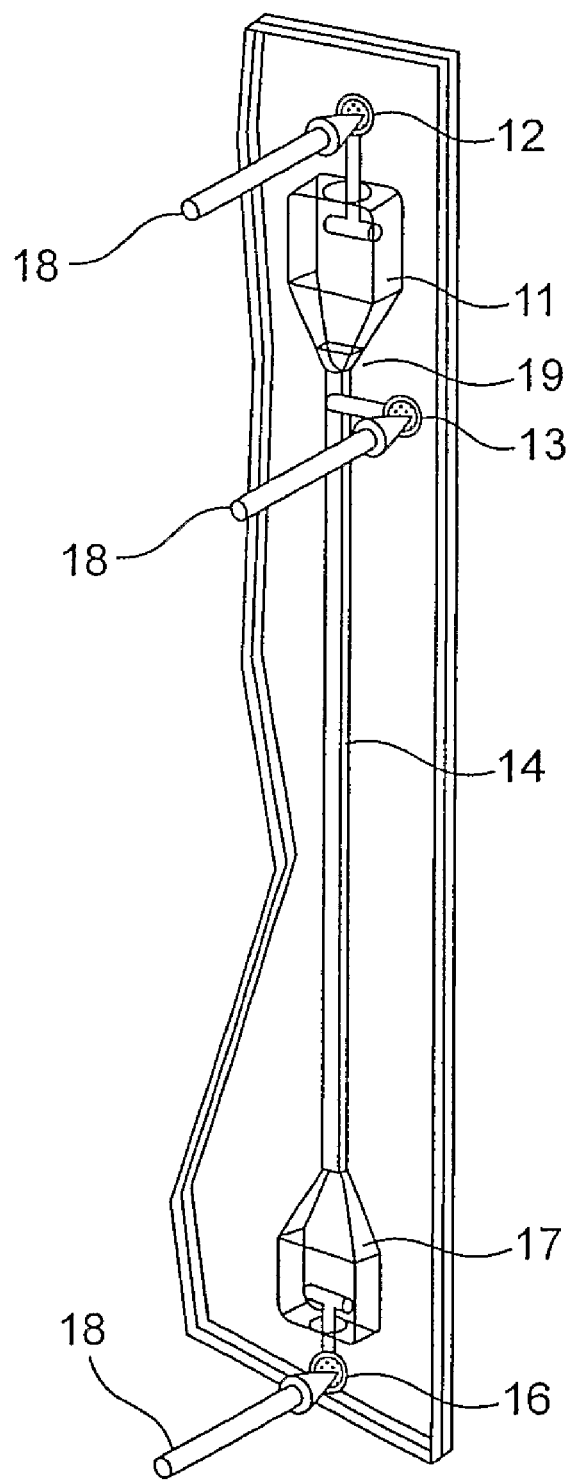
FIG. 18 shows one complete segment of the microfluidic device including illustration of the method of interfacing the external probes.

FIGS. 16 to 18 show further views of a suitable microfluidic device. For the purpose of example, a three layer polymer lamination is shown. A transparent layer 2 incorporates electrode pads 3 on its inner surface and is attached to a process layer 4 that incorporates channel and cavity structures containing chemical reagents, together they comprise the microfluidic assembly 5. A carrier layer 6 supports and protects item 5 and incorporates pockets 7. Access holes 8 through item 4 and 6 allow external electrical probes to interface with electrodes 3. The device is generally planar and is typically processed in a vertical plane such that its upper edge presents loading ports to the processing instrument. In this example, the device has on-board reagents comprising a separation gel 9 which can be pre-loaded with a suitable stainer, for example ethidium bromide, and an electrolytic buffer 10 which fills the top cavity 11 of the microfluidic assembly 5. The electrodes 3 comprise an anode 12 within the top cavity 11, a compacting electrode 13 which crosses the capillary channel 14 immediately above the top of the gel surface 15, and a cathode 16 within the lower cavity 17.

With reference to FIG. 18, bio-molecular separation can be enabled by loading the sample diluted in a low ionic strength buffer and mixed with glycerol which causes the loaded sample to sink under gravity to the lower end of top cavity 11.

Application of a low voltage dc potential (for example 10 volts) between cathode 12 and anode 16 will cause a DNA sample to rapidly migrate to the top of the gel surface 15; this method being the already known method of stacking by use of discontinuous buffers. Sample migration into the gel with this voltage is strongly retarded (due to the higher ionic strength of the gel) for a stacking duration which can be in the range of 5 to 30 seconds.

switch the voltage to a much higher level, for example in the range of 120 to 200 volts, which drives the stacked sample into the gel for separation. A separation column of 20 mm in length will allow separation of a DNA sample in the range 25 to 2000 base pairs when using an agarose gel of 0.8% concentration in typically 60 to 75 seconds.

With reference to FIG. 18, an alternative stacking method is to use the compacting electrode 13 to compact a DNA sample loaded into top cavity 11 by switching top electrode 12 negative and the compacting electrode 13 positive, thereby focussing the sample on the compacting electrode which is preferably gold or platinum or silver thereby avoiding chemical affinity between the electrode and the DNA sample. Typically, the voltage used can be 100V for 20 seconds. The compacting electrode can then be switched off and the positive charge switched to the lower electrode 16 at the other end of the separation channel to separate the sample. Typically this can be 150V for 75 seconds.

FIG. 17b shows an enlargement of the pipette insertion step of FIG. 17a, showing an overspill 112 and the configuration of the flaps 114.

Further features of the microfluidic device are: the embodiment of fiducial marks which can be applied simultaneously with the electrodes 12, 13, and 16 by a process which can conveniently be screen printing, but may also be ink jet, hot foil, flexo print or other similar printing techniques; and the embodiment of a side label which can be used as handling tab during the loading and unloading of the microfluidic device onto or from the instrument and can also be used as an identification label that incorporates useful data such as the device type, use by date, batch code and that this data can be in the form of a 1D or 2D bar code.

It is a function of the analysis instrument to load the test sample into top cavity 11 using a pipette tip 24 after first using a piercing tool 40 to penetrate pocket 7 and cavity 11.

The loaded sample can then be stacked into a narrow band at the top of the gel using techniques for sample stacking in either electrophoresis or column chromatography devices. These include, for example, the use of discontinuous buffers in which the sample is diluted or the transient application to the sample of much lower voltages than those used for sample separation.

With reference to FIG. 18, a further alternative method of utilising the three electrodes is:

apply voltage between electrodes 12 and 16 at low dc voltage (typically in the range 2V to 10V) for a period of approximately 20 seconds to stack the test sample 19 on to the top surface of the gel;

apply voltage between electrodes 12 and 13 (typically 150V for 20 seconds) which results in absorbance of any residual test sample 19 in top cavity 11 into the electrode 13 which specifically is composed of carbon, therefore having a high absorbance for DNA (and therefore avoids smearing during the subsequent separation process from residual DNA in top cavity 11 since this residual material is absorbed); and apply voltage between electrodes 12 and 16 (typically 150V for 60 seconds) to electro-kinetically move and separate the test sample 19 within capillary channel 14.

Excite the test sample stainer (for example, ethidium bromide or cybrgreen) with a light source of appropriate wavelength and capture an image of the capillary channel showing the resulting fluorescence pattern displayed by the separated nucleic acid fragments in channel 14.

Figure 19:
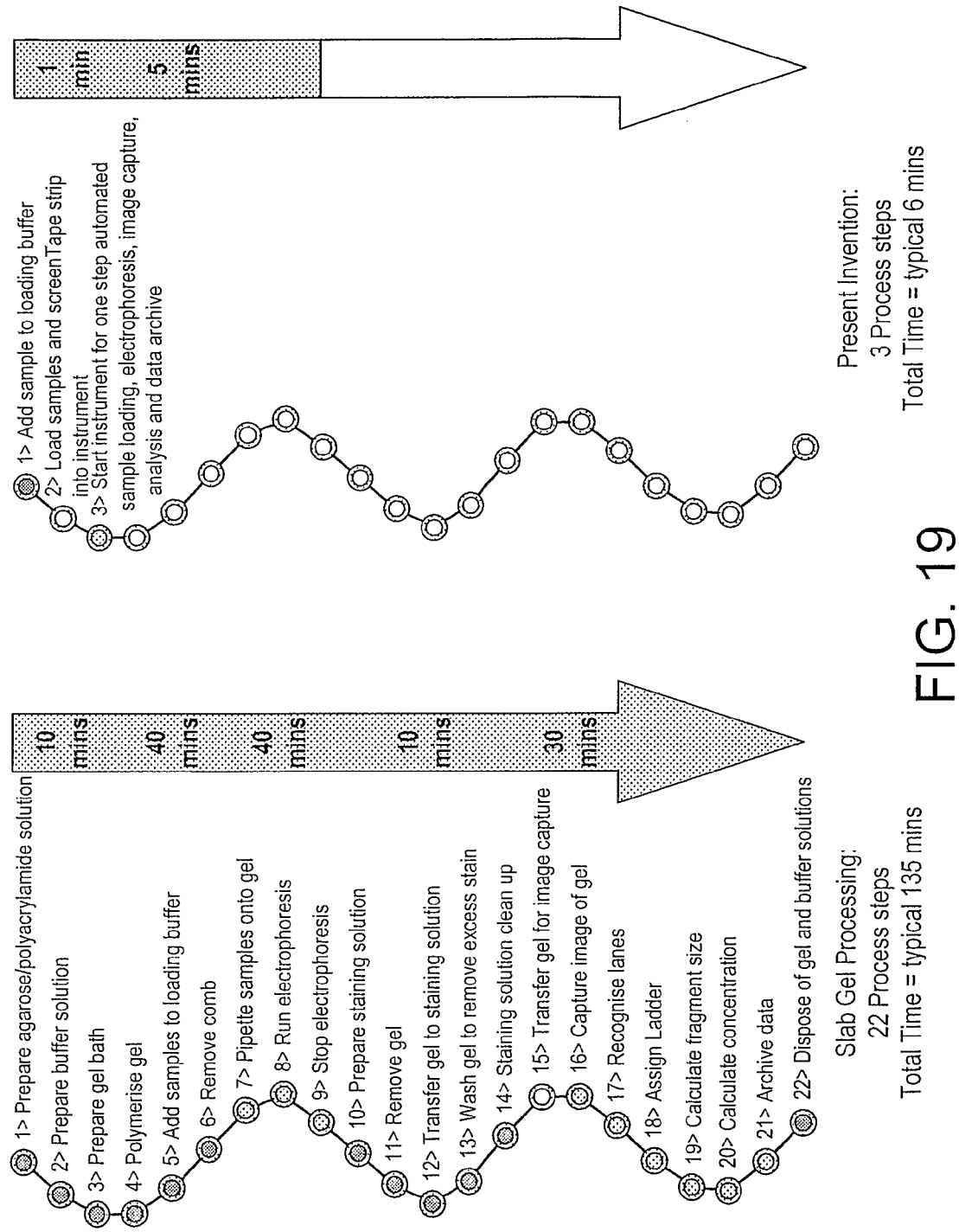
FIG. 19 shows a comparison of slab gel processing and processing using an embodiment of the present invention.

With reference to FIG. 19, the above operating sequence combined with the microscale nature of the microfluidic device combined with the automated handling described in FIGS. 3a and 3b will enable one microfluidic device (which can incorporate up to at least 16 parallel test segments) to be processed in less than six minutes and in three steps. This compares favourably with an equivalent slab gel process which can typically take around 135 minutes involving 22 process steps.

Advantageously, the present invention provides a highly compact, automated, simple to use, rapid and efficient means of providing bio-analysis results, and in particular, when this involves electro-phoretic separation.

Improvements and modifications may be incorporated herein without deviating from the scope of the invention.

What is claimed is:

1. A microfluidic processing device comprising:
   a reaction chamber;
   a carrier layer comprising piercable material;
   a sample loading chamber into which a sample is injectable;
   a piercable process layer; and
   an overspill cavity;
   wherein the sample loading chamber is formed between the reaction chamber, which is operatively connected to the sample loading chamber, and the piercable process layer; and
   wherein the overspill cavity is formed from a space between the piercable process layer and the carrier layer and configured to accept any overspill.

2. A microfluidic processing device according to claim 1, wherein the carrier layer and the piercable process layer are components of a laminated structure.

3. A microfluidic processing device according to claim 1, wherein the reaction chamber comprises a molecular separation medium.

4. A microfluidic processing device according to claim 3, wherein the carrier layer and/or the piercable process layer are manufactured from polymer film.

5. A microfluidic processing device according to claim 3, including optical fiducial marks having known positions relative to the reaction chamber and which can be acquired by a detection means of an analysis instrument to accurately identify a position of a reaction process.

6. A microfluidic processing device according to claim 3, wherein the reaction chamber is a channel.

7. A microfluidic processing device according to claim 6, wherein the microfluidic processing device further includes a receiving chamber at an end of the reaction channel remote from the sample loading chamber.

* * * * *

UNITED STATES PATENT AND TRADEMARK OFFICE
CERTIFICATE OF CORRECTION

| | | |
|---|---|---|
| PATENT NO. | : 8,101,137 B2 | Page 1 of 1 |
| APPLICATION NO. | : 11/815852 | |
| DATED | : January 24, 2012 | |
| INVENTOR(S) | : Stuart Polwart et al. | |

It is certified that error appears in the above-identified patent and that said Letters Patent is hereby corrected as shown below:

On the Title Page, Item (75), in "Inventors", in column 1, line 2, delete "Peebleshire" and insert -- Peeblesshire --, therefor.

In column 16, line 4, in Claim 1, delete "piercable" and insert -- pierceable --, therefor.

In column 16, line 7, in Claim 1, delete "piercable" and insert -- pierceable --, therefor.

In column 16, line 11, in Claim 1, delete "piercable" and insert -- pierceable --, therefor.

In column 16, line 14, in Claim 1, delete "piercable" and insert -- pierceable --, therefor.

In column 16, line 17, in Claim 2, delete "piercable" and insert -- pierceable --, therefor.

In column 16, line 23, in Claim 4, delete "piercable" and insert -- pierceable --, therefor.

Signed and Sealed this
Eleventh Day of December, 2012

David J. Kappos
*Director of the United States Patent and Trademark Office*